United States Patent
Ueda et al.

(10) Patent No.: US 10,220,199 B2
(45) Date of Patent: Mar. 5, 2019

(54) VALVE BODY AND CONNECTOR INCLUDING THE SAME

(71) Applicant: TERUMO KABUSHIKI KAISHA, Shibuya-ku, Tokyo (JP)

(72) Inventors: Yasuhiro Ueda, Kofu (JP); Yoshikazu Hama, Tottori (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 76 days.

(21) Appl. No.: 14/668,118

(22) Filed: Mar. 25, 2015

(65) Prior Publication Data
US 2015/0196750 A1 Jul. 16, 2015

Related U.S. Application Data

(63) Continuation of application No. PCT/JP2012/075017, filed on Sep. 28, 2012.

(51) Int. Cl.
*A61M 39/26* (2006.01)
*F16K 27/00* (2006.01)
(Continued)

(52) U.S. Cl.
CPC .......... *A61M 39/26* (2013.01); *A61M 39/045* (2013.01); *A61M 39/223* (2013.01);
(Continued)

(58) Field of Classification Search
CPC .. A61M 2039/2426; A61M 2039/0235; A61M 2039/2433; A61M 39/24; A61M 29/263
See application file for complete search history.

(56) References Cited

U.S. PATENT DOCUMENTS 6,171,287 B1 * 1/2001 Lynn .............. A61M 39/02
251/149
7,306,579 B2 * 12/2007 Fujii .............. A61M 39/045
604/244
(Continued)

FOREIGN PATENT DOCUMENTS

JP 2002/306610 A 10/2002
JP 2003-144546 A 5/2003
(Continued)

OTHER PUBLICATIONS

"Portion." Merriam-Webster.com. Merriam-Webster, n.d. Web. Jun. 30, 2017.*
International Search Report (PCT/ISA/210) dated Jan. 8, 2013, by the Japanese Patent Office as the International Searching Authority for International Application No. PCT/JP2012/075017.

*Primary Examiner* — Nathan R Price
*Assistant Examiner* — Courtney B Fredrickson
(74) *Attorney, Agent, or Firm* — Buchanan Ingersoll & Rooney PC

(57) ABSTRACT

A connector is disclosed, which includes a main body and a valve body. The main body can include a main line flow channel capable of circulating an infusion solution, and valve body arrangement portions and connecting to the main line flow channel. The valve body includes an operable and closable slit provided to a deformed portion. The valve body is provided along an opening/closing direction of the slit, and includes a guide portion configured to facilitate opening and closing of the slit, and a thickened portion protrusively formed so as to extend through near both ends in a longitudinal direction of the slit and on both sides of the guide portion.

20 Claims, 7 Drawing Sheets

(51) Int. Cl.
*A61M 39/22* (2006.01)
*F16K 27/04* (2006.01)
*A61M 39/04* (2006.01)
*A61M 39/00* (2006.01)

(52) U.S. Cl.
CPC .............. *F16K 27/00* (2013.01); *F16K 27/04* (2013.01); *A61M 2039/0072* (2013.01); *A61M 2039/0081* (2013.01); *A61M 2206/20* (2013.01)

(56) References Cited

U.S. PATENT DOCUMENTS

2007/0218745 A1    9/2007  Yokota et al.
2007/0244426 A1*  10/2007  Hart .................. A61B 17/3462
                                                            604/30
2008/0132832 A1*   6/2008  McKinnon .......... A61M 39/045
                                                         604/93.01
2010/0007134 A1    1/2010  Elton et al.
2010/0063440 A1*   3/2010  Kitani ................. A61M 39/045
                                                            604/83

FOREIGN PATENT DOCUMENTS

| JP | 2004-105574 A | 4/2004 |
| JP | 3719443 B2 | 11/2005 |
| JP | 2010-167202 A | 8/2010 |
| JP | 4744440 B2 | 8/2011 |
| WO | WO 02/064077 A1 | 8/2002 |
| WO | WO 2004/101061 A1 | 11/2004 |

\* cited by examiner

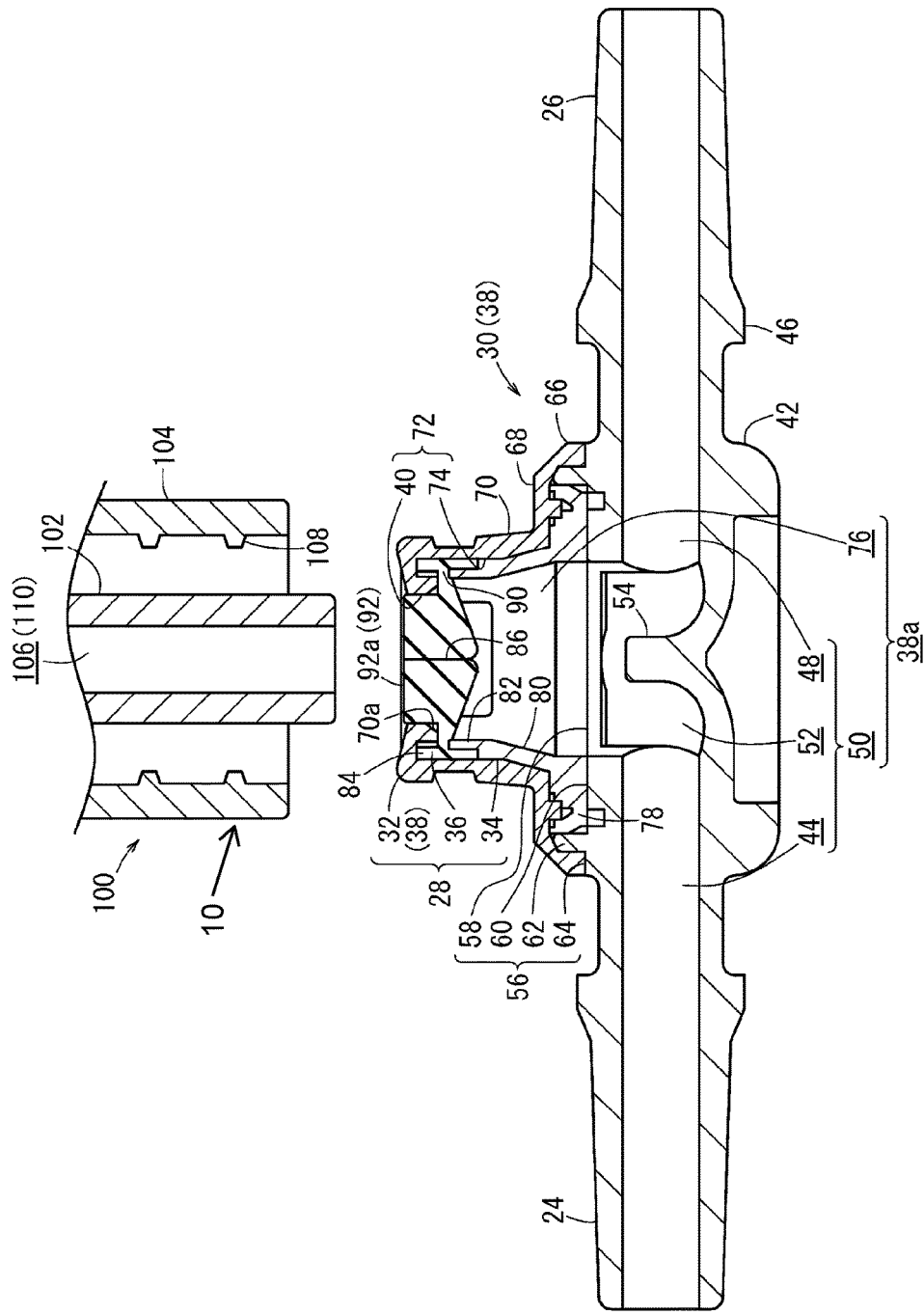

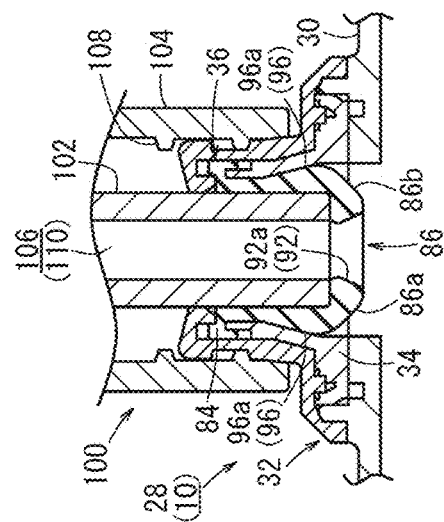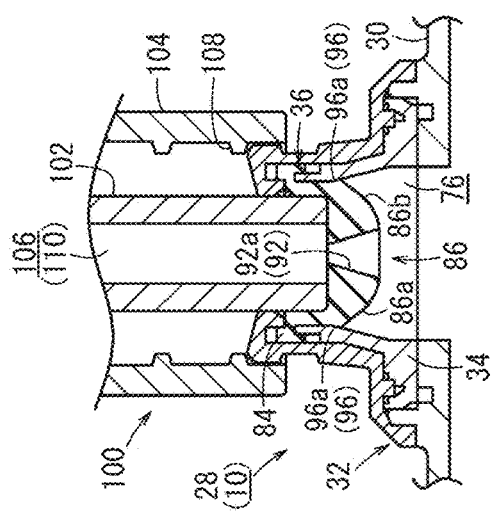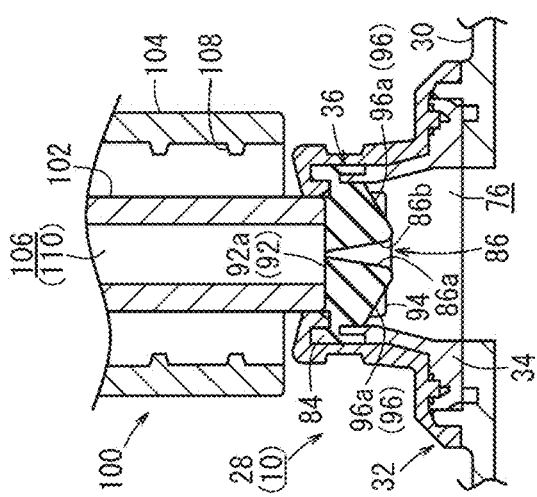

VALVE BODY AND CONNECTOR INCLUDING THE SAME

CROSS-REFERENCES TO RELATED APPLICATIONS

This application is a continuation of International Application No. PCT/JP2012/075017 filed on Sep. 28, 2012, the entire content of which is incorporated herein by reference.

TECHNICAL FIELD

The present disclosure generally relates to a valve body configured to circulate and block a fluid with opening and closing a slit, and a connector including the valve body.

BACKGROUND DISCUSSION

Conventionally, when an infusion solution is administered to a patient, an infusion line is constructed by connecting multiple tubes from an infusion bag to the patient, and the multiple tubes are interconnected through a connector. In infusion, in addition to a main line for feeding a main infusion solution to a patient, another infusion solution may be fed from a line different from the main line, and the solutions are fed to the patient after being mixed at a connector. The connector used in this case has three directions port capable of mixing multiple infusion solutions (see JP 2010-167202 A).

A connector (medical port) disclosed in JP 2010-167202 A includes a connection port connected to a male connector (insertion body) on a separate line in addition to two ports including a main line. In the connection port, a slit (insertion hole) opens and closes with inserting and separating the male connector, and a valve body configured to circulate and block a fluid is provided. To prevent breaking of the slit by insertion of the male connector, the valve body includes a ring-shaped protrusion (FIG. 8 in JP 2010-167202 A) formed so as to surround the slit or a protrusion (FIG. 10 in JP 2010-167202 A) protrusively formed at both ends in a longitudinal direction of the slit.

However, in the valve body in which a ring-shaped protrusion is formed in a vicinity of the slit, the strength of the slit in an opening/closing direction is increased by the ring-shaped protrusion. Therefore, when a male connector is inserted into the valve body, an inconvenience occurs that the slit is hard to open. Even if a protrusion is provided at an end in a longitudinal direction of the slit to ensure openability, the strength of the valve body can be decreased. Consequently, another issue occurs that the valve body cannot withstand multiple times usage and can be relatively easily damaged.

SUMMARY

In accordance with an exemplary embodiment, a valve body and a connector including the valve body are disclosed, and wherein durability of the valve body can be enhanced by a relatively simple configuration, and the valve body can easily open while an insertion body is inserted in the valve body.

In accordance with an exemplary embodiment, a connector is disclosed, which can include a main body including a flow channel capable of circulating a fluid, and a space connecting to the flow channel, and a valve body including a base body displaceably provided to the space and a slit capable of opening and closing with respect to the flow channel based on elastic deformation of the base body. The valve body is provided at a bottom of the base body along an opening/closing direction of the slit. The valve body can include a guide portion configured to facilitate opening and closing of the slit and a thickened portion protrusively formed so as to extend through near both ends in a longitudinal direction of the slit and on both sides of the guide portion.

In accordance with an exemplary embodiment, the valve body can be provided along an opening/closing direction of the slit and can include a guide portion configured to facilitate opening and closing of the slit. Accordingly, the slit smoothly opens along the guide portion when a male connector is connected to a connector. As a result, the connector can promptly circulate a fluid when the male connector is connected thereto, and insertability of the male connector can be improved. In addition, the valve body can include a thickened portion protrusively formed so as to extend through near both ends in a longitudinal direction of the slit and on both sides of the guide portion. Accordingly, entire durability of the valve body can be improved, and damage on the valve body can be substantially suppressed. For example, since the thickened portion is disposed in a vicinity of both ends in a longitudinal direction of the slit, the thickened portion can help successfully prevent breaking of the slit in the longitudinal direction.

In this case, in the guide portion a wall thickness on an outer side in an opening/closing direction of the slit is preferably thinner than a wall thickness around a portion where the slit is formed.

Openability of the slit can be easily improved by including the guide portion in which the wall thickness on the outer side in the opening/closing direction of the slit is thinner than the wall thickness around the portion where the slit is formed. For example, a wall of the valve body can be easily moved to a thin wall side by elastic deformation. Therefore, a wall around the portion where the slit is formed is moved to the outer side in the opening/closing direction, and accordingly the slit opens. In addition, when the slit is closed, a fluid flowing into a space can apply a stress from a thin wall side to a thick wall side of the valve body, and accordingly the slit is positively closed.

In addition, the guide portion can be preferably formed in a tapered shape in which a wall thickness of the valve body is gradually reduced toward the outer side in the opening/closing direction from the slit.

Since the guide portion is formed in a tapered shape, while the slit is opened, tapered bottoms of the valve body in the tapered shape can be elastically deformed to separate each other, and opening and closing of the slit is further facilitated. In addition, when the slit is closed, a fluid flowing into the space can apply a fluid pressure on a whole surface of the guide portion formed in a tapered shape, and the slit can be more firmly closed.

The thickened portion preferably includes a wall linearly extending in a direction perpendicular to a longitudinal direction of the slit.

As a result, opening and closing of the slit can be guided along the wall. If the slit breaks in a direction different from a longitudinal direction of the slit, the linearly extending wall can easily block the break.

In accordance with an exemplary embodiment, a valve body is disclosed, which can include a base body, a slit, a guide portion, and a thickened portion. The slit is openable and closable and provided to the base body. The guide portion is provided along an opening/closing direction of the slit and facilitates opening and closing of the slit. The thickened portion is protrusively formed so as to extend through near both ends in a longitudinal direction of the slit and on both sides of the guide portion.

BRIEF DESCRIPTION OF DRAWINGS

FIG. 4 is a side sectional view of the connector illustrated in FIG. 2.

FIG. 6A is a first explanatory view illustrating a connection operation between the connector and a male connector illustrated in FIG. 4.

FIG. 6B is a second explanatory view illustrating a connection operation between the connector and the male connector illustrated in FIG. 4.

FIG. 6C is a third explanatory view illustrating a connection operation between the connector and the male connector illustrated in FIG. 4.

DETAILED DESCRIPTION

Hereinafter, a valve body according to the present invention and a connector including the valve body will be described in detail based on a relation with an infusion set applicable to the connector, and the connector is not limited to an application to the infusion set.

Figure 1:
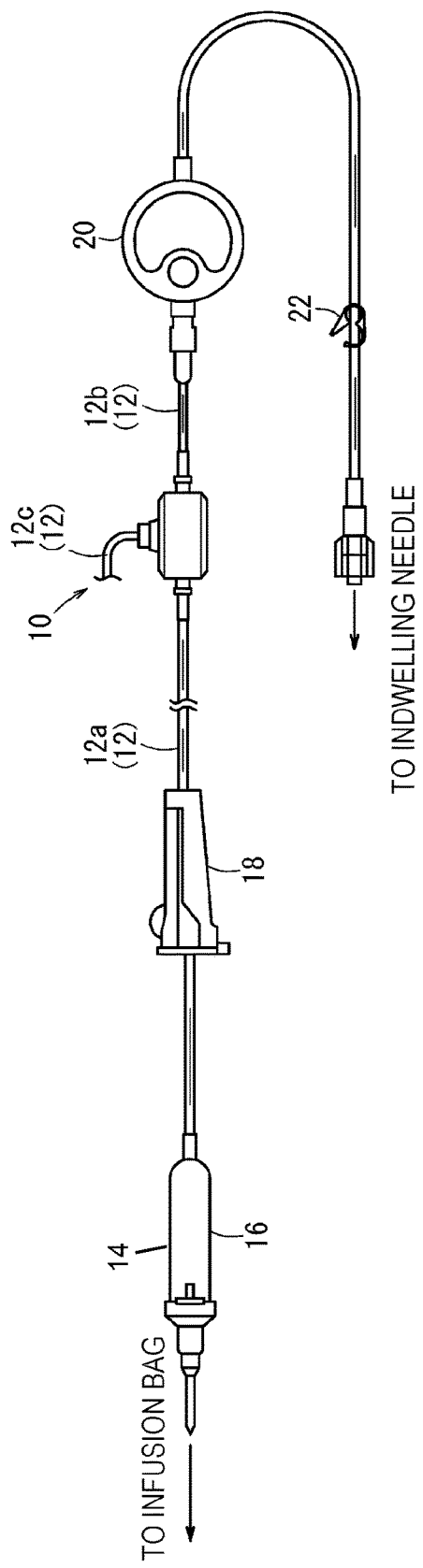
FIG. 1 is an explanatory view schematically illustrating an example of an infusion set in which a connector according to a present embodiment is applied.

As described above, a connector 10 has a function to connect multiple tubes 12 to each other on an infusion line for transfusing to a patient. For example, the function is applicable to an infusion set 14 illustrated in FIG. 1. In the infusion set 14, an upper stream side is connected to an infusion bag (not illustrated), a downstream side is connected an indwelling needle (not illustrated). Thus, an infusion line for administering an infusion solution from the infusion bag to a patient is constructed.

Examples of infusion solutions circulating in the infusion set 14 can include various fluids, which can be administered to a living body, such as a medicinal solution, an electrolyte solution for correction, and a normal saline solution. In addition, in the case where the infusion solution is a medicinal solution, the medicinal solution can be chosen from various medical agents such as a pain reliever, an intravenous anesthetic, a narcotic analgesic, a local analgesic, a nondepolarizing muscle relaxant, a hypertensive drug, a antihypertensive drug, a coronary vasodilator, a diuretic, an antiarrhythmic drug, a bronchodilator, a styptic, a vitamin preparation, an antibiotic, and a fat emulsion.

The tubes 12 in the infusion set 14 can include, for example, a drip chamber 16, a drip clamp 18, an air vent filter 20, and a clamp 22. The drip chamber 16 can visualize a flow amount of an infusion solution supplied from an infusion bag. The drip clamp 18 adjusts the flow amount of the infusion solution. The air vent filter 20 discharges (or supplies) air in the infusion line. The clamp 22 closes the tubes 12. In accordance with an exemplary embodiment, the infusion set 14 is not limited to a configuration illustrated in FIG. 1, and various members provided on an infusion line (for example, an infusion pump and a backflow preventive valve) can be applied other than the members described above.

The tubes 12 in the infusion set 14 can be a flexible pipe body and can include a flow channel for an infusion solution. If the connector 10 is applied to the above infusion set 14, the connector 10 can be disposed, for example, between the drip pinchcock 18 and the air vent filter 20. For example, the connector 10 can be communicatively connected between a first tube 12a extending from the drip chamber 16 to a downstream side and a second tube 12b extending to an upper stream side of the air vent filter 20. In addition, the connector 10 can be a three-port connector, which can connect to a third tube 12c as a line different from a main line including the first tube 12a and the second tube 12b.

The connector 10 is not limited to being disposed at the above-described location, and can be disposed at a desired location in the infusion set 14. For example, a plurality of the connectors 10, not just one, may be provided in the infusion set 14 (infusion line).

Figure 2:
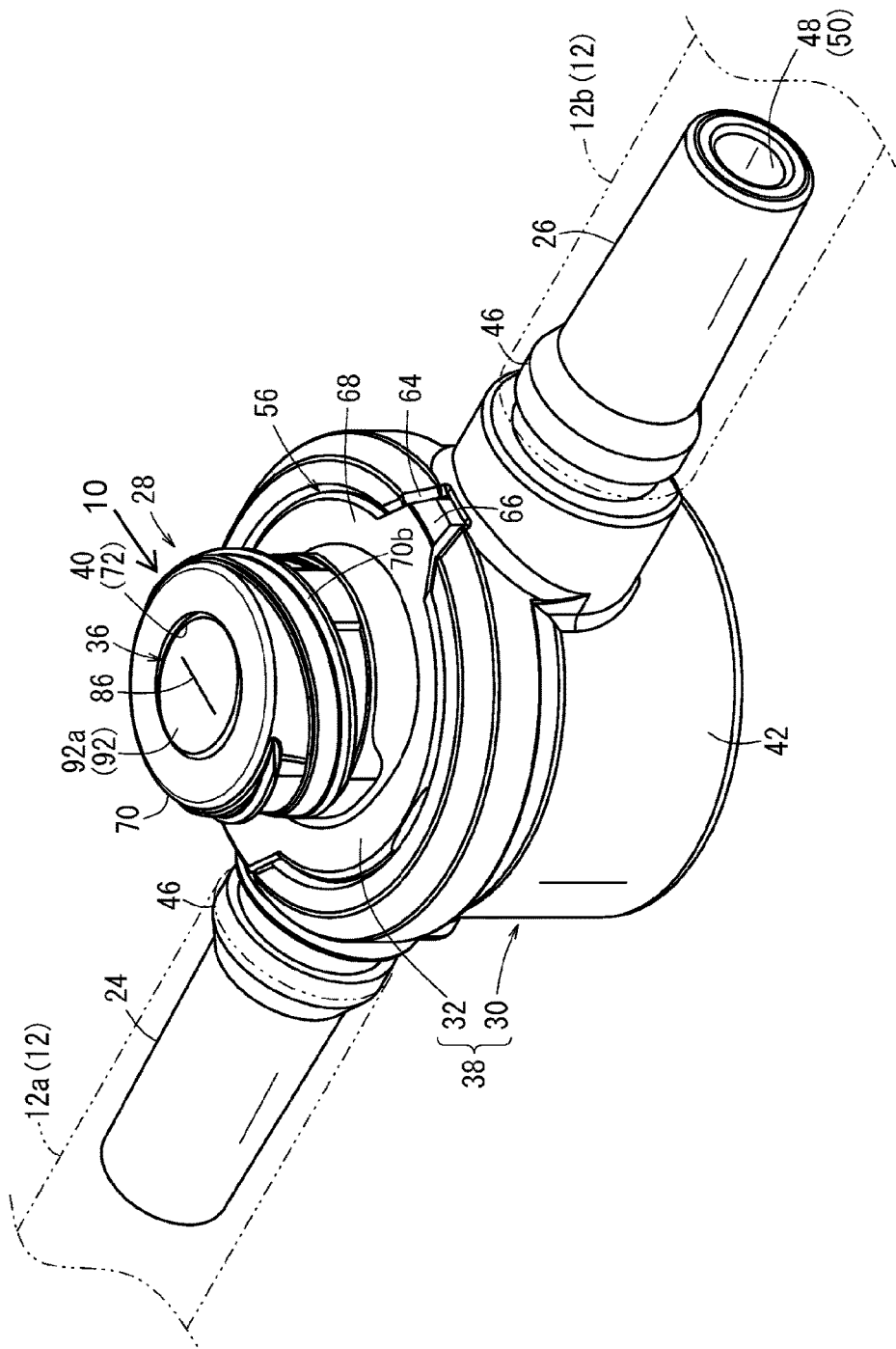
FIG. 2 is a perspective view illustrating a whole configuration of the connector illustrated in FIG. 1.
Figure 3:
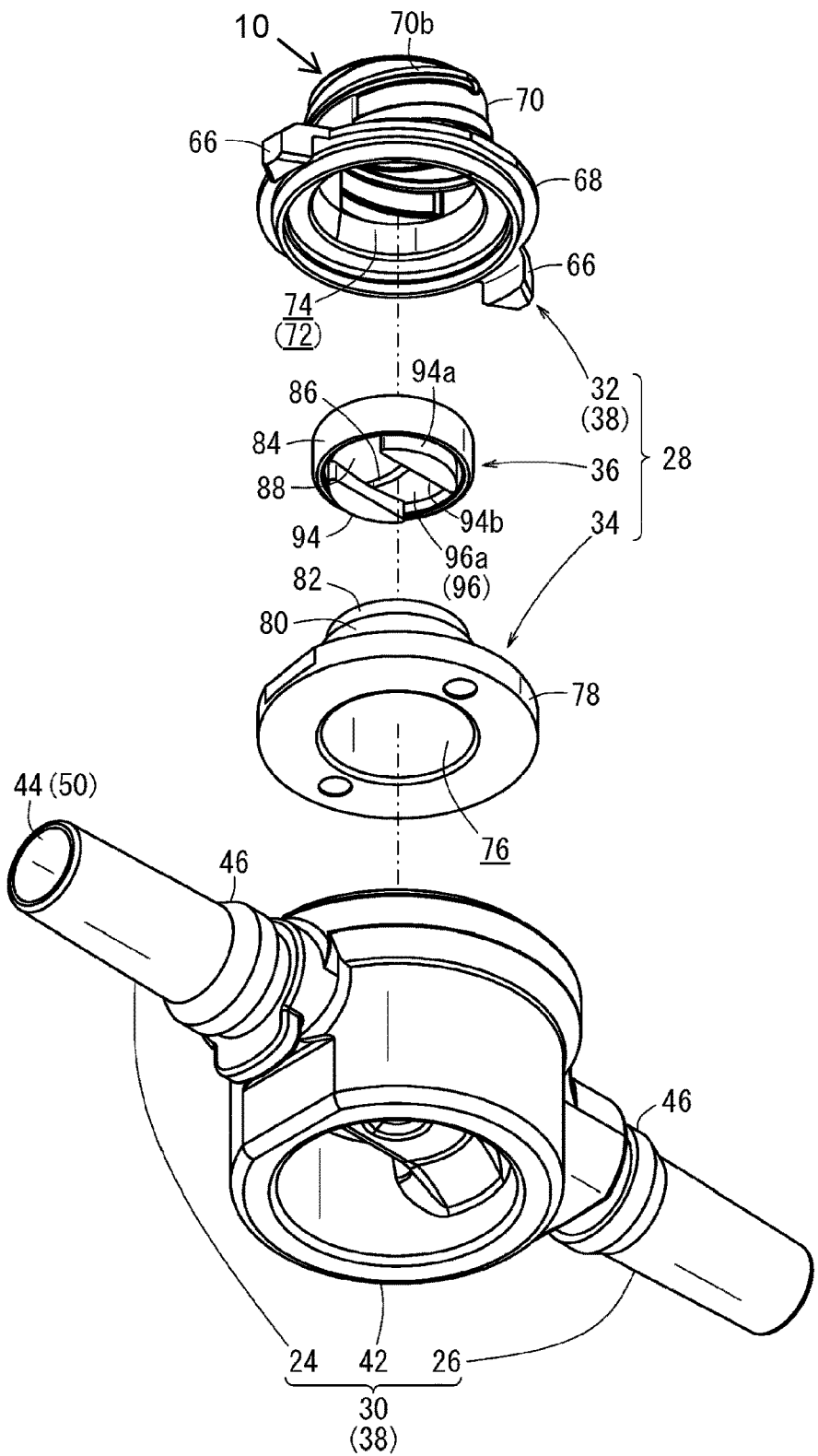
FIG. 3 is an exploded perspective view of the connector illustrated in FIG. 2.
Figure 5B:
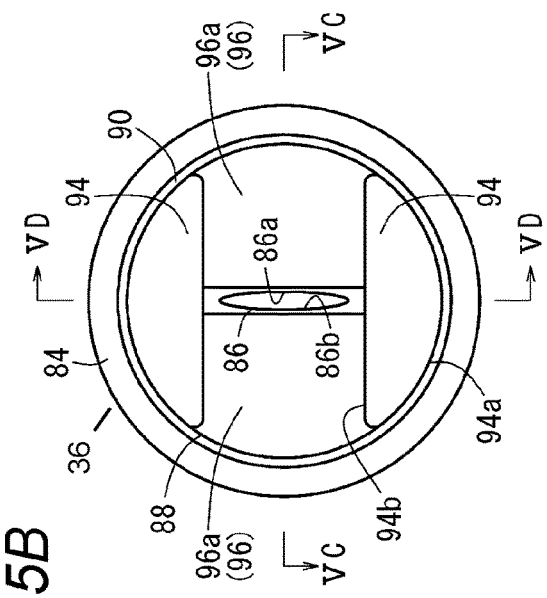
FIG. 5B is a bottom view for describing the valve body of the connector illustrated in FIG. 2.
Figure 5D:
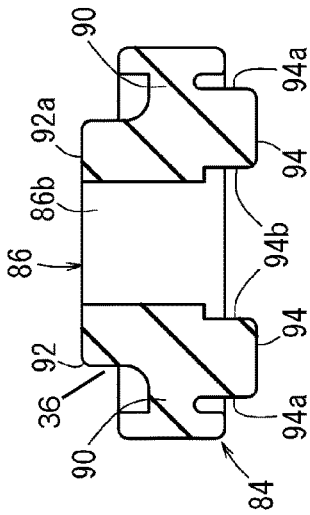
FIG. 5D is a sectional view on line VD-VD illustrated in FIG. 5B.
Figure 5A:
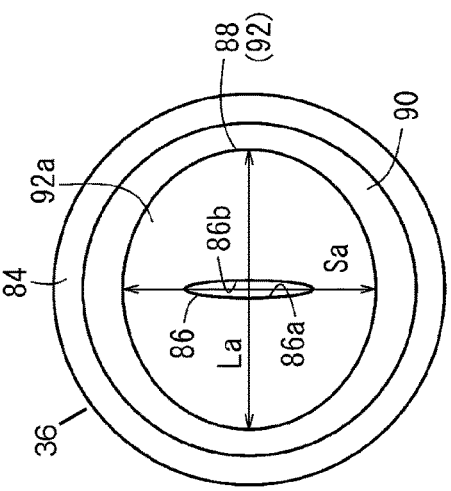
FIG. 5A is a plan view for describing a valve body of the connector illustrated in FIG. 2.
Figure 5C:
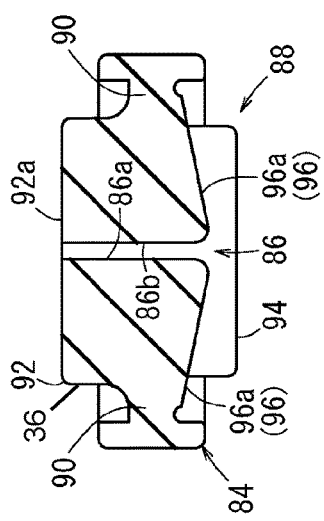
FIG. 5C is a sectional view on line VC-VC illustrated in FIG. 5B.

Hereinafter, an exemplary configuration of the connector 10 according to the present embodiment will be described in detail. As illustrated in FIGS. 2 to 4, the connector 10 can include a first port 24, a second port 26, and a third port 28. A first tube 12a included in a main line is connected to the first port 24. A second tube 12b also included in the main line is connected to the second port 26. A third tube 12c included in a line different from the main line is connected to the third port 28. The first and second ports 24 and 26 can be provided in a housing 30 including a flow channel for an infusion solution therein. The third port 28 can include a cap 32, which is a member different from the housing 30, a support body 34, and a valve body 36. Each of the members is assembled to the housing 30.

The housing 30 and the cap 32 can be connected to each other and configured as a main body 38 of the connector 10 including a flow channel 38a for an infusion solution therein the flow channel 38a. The support body 34 and the valve body 36 can be stored in the main body 38. An upper surface of the valve body 36 is exposed from an opening 40 of the cap 32.

The housing 30, the cap 32, and the support body 34 in the connector 10 can be formed by a resin material from an aspect of simplification of and cost reduction in a molding process. In accordance with an exemplary embodiment, the resin material preferably has higher rigidity than that of the tubes 12. Examples of the resin material include polyethylene, polypropylene, ethylene-vinyl acetate copolymer polyolefin, polyurethane, polyamide, polyester, polycarbonate, polybutadiene, and polyvinyl chloride.

The housing 30 can include a bottomed cylindrical connector base 42 at a center of the housing 30. The first and second ports 24 and 26 can be connected on a side peripheral surface of the connector base 42. The first port 24 can be formed in a substantially cylindrical shape and linearly extending from the connector base 42 toward an upper stream side of the main line. A first port flow channel 44 capable of circulating an infusion solution is extended along an axial direction in the first port 24.

The first port 24 can be configured as a male luer taper gradually tapering toward an extended end and inserted into a tube (lumen) of the first tube 12a. In addition, a protruding portion 46 can be formed along a circumferential direction on an outer peripheral surface in a vicinity of the connector base 42 in the first port 24. The first tube 12a and the first port 24 can be liquid-tightly connected by inserting the first tube 12a over the protruding portion 46.

In accordance with an exemplary embodiment, the second port 26 can be formed in the same shape as the first port 24 on an opposite side of the first port 24 across the connector base 42, and linearly extended from the connector base 42 toward a downstream side of the main line. A second port flow channel 48 capable of circulating an infusion solution can be extended along an axial direction in the second port 26. For example, the first and second ports 24 and 26 can be formed so that axes of the first and second ports 24, 26 coincide with each other and linearly line up. Accordingly, the first and second port flow channels 44 and 48 are linearly connected with each other. The linearly connecting first and second port flow channels 44 and 48 are a flow channel of the main line (hereinafter called "a main line flow channel 50") in the connector 10. The main line flow channel 50 is capable of smoothly circulating a first infusion solution flowing therein.

The bottomed cylindrical connector base 42 has a thickness supporting a connection between the first port 24 and the second port 26 on a side peripheral surface thereof. As illustrated in FIG. 4, an internal flow channel 52 connecting between the first port flow channel 44 and the second port flow channel 48 is formed in the connector base 42. The internal flow channel 52 can be a part of the main line flow channel 50 and extended so as to linearly connect the main line flow channel 50. In addition, a guide wall 54 for guiding circulation of the first infusion solution in a vertical direction (a connecting direction of the cap 32) is formed at a center in an axial direction of the internal flow channel 52.

An upper side of the connector base 42 is configured as an attachment unit 56 for attaching the cap 32 and the support body 34. The attachment unit 56 can include a round-shaped exposure opening 58, an arrangement portion 60, a hook wall 62, and a groove 64. The round shaped exposure opening 58 is formed by notching an upper surface of the connector base 42 in a round shape and exposes the internal flow channel 52 at a center. The arrangement portion 60 is formed in a flat shape and surrounds around the exposure opening 58. The hook wall 62 and the groove 64 are formed on bases of the first and second ports 24 and 26 on an outer side of the arrangement portion 60. The arrangement portion 60 can include the support body 34. On the hook wall 62, a locking claw 66 of the cap 32 is configured to be locked to the hooking wall 62.

As described above, the third port 28 is a connection terminal including the cap 32, the support body 34, and the valve body 36. The third port 28 is provided in an orthogonal direction against an axial direction of the first and second ports 24 and 26 by fixedly connecting to the attachment unit 56. For example, the connector 10 is configured as a T-port connector in which a branch angle of the third port 28 with respect to the main line flow channel 50 is 90°. The third port 28 flows a second infusion solution supplied from the third tube 12c into the internal flow channel 52 and converges the second infusion solution with the first infusion solution in the connector 10.

The valve body 36 is stored in the cap 32, and the cap 32 is formed in a shape connectable to a male connector 100 of the third tube 12c. The cap 32 can include a flange 68 on a lower side connected to the connector base 42, and a terminal unit 70 extending upward from the flange 68 for a predetermined length.

The flange 68 is formed on an outer diameter covering the arrangement portion 60 of the connector base 42. A pair of the locking claws 66 projecting on an outer side in a radial direction is connected at a predetermined symmetry position on a peripheral edge of the flange 68 sandwiching the terminal unit 70. A pair of the locking claws 66 is formed in a hook shape of which interval therebetween is slightly shorter than that of a pair of the hook walls 62, and configured so as to hook into the hook wall 62 by being inserted in the groove 64 of the connector base 42.

The terminal unit 70 is formed in a cylindrical shape having a diameter smaller than the flange 68, and a hole 72 is formed along an axis direction (vertical direction) in the terminal unit 70. The opening 40 narrowing toward an inner side in a radial direction is formed on an upper side of the hole 72. A storage 74, which has a diameter larger than the opening 40 and can store the support body 34 and the valve body 36, is provided on a lower side of the opening 40. The opening 40 has a predetermined inner diameter (an inner diameter in which the valve body 36 can be inserted) by being surrounded by a ring-shaped protruding portion 70a projecting from an upper edge to a lower side of the terminal unit 70. In addition, a helical ridge 70b is formed on an outer peripheral surface of the terminal unit 70. The male connector 100 of the third tube 12c is screwed together with the ridge 70b.

In accordance with an exemplary embodiment, the male connector 100 of the third tube 12c connected to the connector 10 as a separate line in the infusion set 14 will be described with reference to FIG. 4. The male connector 100 is connected to the connector 10, for example, by using a luer lock type connector. For example, a connector having a shape standardized in ISO can be preferably used. For example, the male connector 100 is formed in a double cylindrical shape including an insertion cylinder 102 to be inserted into the connector 10 (the cap 32) and a connection cylinder 104 surrounding around the insertion cylinder 102 and capable of being screwed together with the ridge 70b of the cap 32.

The insertion cylinder 102 projects for a predetermined length from an opening end of the connection cylinder 104 and pushes out a slit 86 of the valve body 36 when the male connector 100 is connected. A flow path 106 capable of circulating the second infusion solution supplied from the third tube 12c in the insertion cylinder 102. The flow path 106 is configured as a flow channel on a separate line (hereinafter called a "separate line flow channel 110").

The connection cylinder 104 has a predetermined gap between the insertion cylinder 102 and the connection cylinder 104, and a projection 108 projected inward and formed in a spiral shape is provided on an inner peripheral surface thereof. For example, the male connector 100 can be connected to the third port 28 (the cap 32, the support body 34, and the valve body 36) of the connector 10 by screwing together with the projection 108 of the connection cylinder 104 and the ridge 70b of the cap 32.

In accordance with an exemplary embodiment, the support body 34 of the third port 28 has a function to support so that the internal flow channel 52 and the valve body 36 are positioned so as to be separated for a predetermined interval. For example, a space for inserting the male connector 100 (insertion cylinder 102) over a certain length can be needed to connect between the third port 28 and the male connector 100. The support body 34 supports the valve body 36 at an upper portion thereof, and also creates the space by a vertically extending through hole 76.

The support body 34 can include a brim 78, which is arranged to the arrangement portion 60 of the connector base 42, and a support cylinder 80 protruding upward from an upper surface of the brim 78. In addition, an outer diameter of an upper portion of the support cylinder 80 is a holding portion 82 of which diameter is smaller than a body of the support cylinder 80. In accordance with an exemplary embodiment, a fixed portion 84 of the valve body 36 can be inserted into an outer side of the holding portion 82.

The through hole 76 is formed through in the brim 78 and the support cylinder 80. The through hole 76 connects with the exposure opening 58 in a state in which the support body 34 is arranged at the arrangement portion 60. For example, the through hole 76 is configured as a flow channel in the third port 28, and circulates the second infusion solution from the separate line flow channel 110 to the main line flow channel 50. The flow channel 38a in the main body 38 includes the first and second port flow channels 44 and 48, the internal flow channel 52, and the through hole 76. In addition, the insertion cylinder 102 and the elastically-deformed valve body 36 can be movable with inserting the insertion cylinder 102 in the through hole 76. The through hole 76 and the opening 40 are configured as a space allowing displacement of the valve body 36.

The valve body 36 of the third port 28 is molded with an elastic material different from other materials, and therefore the valve body 36 has an elastic force capable of elastic deformation by inserting the male connector 100. Examples of an elastic material configuring the valve body 36 include, but are not limited to, polybutadiene, nitrile, and chloroprene synthetic rubber, natural rubber such as polyisoprene, thermoset elastomer such as urethane rubber, silicon rubber, and fluoro-rubber, thermoplastic elastomer, or other elastomer.

As illustrated in FIGS. 5A to 5D, the valve body 36 is provided at a center of the slit 86 which opens and closes based on insertion and separation of the male connector 100, and has a function to connect and block the separate line flow channel 110 by opening and closing the slit 86. The valve body 36 is formed in a disk shape having a relatively thick wall. The valve body 36 can include a fixed portion 84 sandwiched between the cap 32 and the support body 34 on an outer side and a deformed portion 88 (base body) connected to the fixed portion 84 on an inner side. The slit 86 is linearly formed so as to vertically penetrate through the deformed portion 88. The deformed portion 88 includes a pair of slit walls 86a and 86b, which forms the slit 86 and can separate and contact each other based on elastic deformation.

The fixed portion 84 is circularly formed so as to surround the deformed portion 88 and has a predetermined thickness in a vertical direction. A constricted portion 90, of which wall thickness is thinner than that of the fixed portion 84, is formed between the fixed portion 84 and the deformed portion 88.

As illustrated in FIG. 4, the holding portion 82 of the support body 34 enters into the constricted portion 90 to support a bottom inside of the fixed portion 84. The cap 32 covers an upper portion and an outer peripheral surface of the fixed portion 84. In addition, the protruding portion 70a enters into the constricted portion 90. Thus, an arrangement position (height) of the valve body 36 in the through hole 76 is defined by sandwiching the fixed portion 84 along a circumferential direction between the cap 32 and the support body 34.

As illustrated in FIGS. 5A to 5D, in a state in which the deformed portion 88 is not stored in the cap 32, the deformed portion 88 has a short axis Sa on an extending direction side (longitudinal direction) of the slit 86 and is formed in an elliptical shape having a long axis La in a direction perpendicular to a longitudinal direction of the slit 86. In addition, in the state in which the deformed portion 88 is not stored in the cap 32, the slit 86 opens (a pair of the slit walls 86a and 86b separate each other.) based on the elliptical shape of the deformed portion 88.

In accordance with an exemplary embodiment, the slit 86 is formed based on a mold shape during injection molding of the valve body 36 and not cut into after the injection molding. By injection-molding the slit 86 and the valve body 36 at the same time, the slit 86 can be formed at a more accurate position, and a process to separately form the slit 86 can be skipped. When the valve body 36 is stored in the opening 40, the ellipsoidal long axis La is roundly shaped by being pushed inside by the protruding portion 70a including the opening 40. Accordingly, a pair of the slit walls 86a and 86b is in close contact with each other, and the slit 86 is closed. In addition, if the deformed portion 88 is pushed down from the opening 40 of the cap 32 by inserting the male connector 100, the slit 86, which has been closed, is positively opened.

The deformed portion 88 can include an upper side swelling portion 92 formed on an upper surface side of the valve body 36, and a thickened portion 94 and a guide portion 96, which are formed on a lower surface side (a bottom surface) of the valve body 36. The slit 86 is formed so as to vertically penetrate through between the upper side swelling portion 92 and the guide portion 96.

The upper side swelling portion 92 on the upper surface side has an outer diameter slightly smaller than a diameter of the opening 40 of the cap 32. In addition, the upper side swelling portion 92 is formed in a column shape protruding upward from the constricted portion 90 for a predetermined amount to increase a wall thickness of the deformed portion 88. The upper surface 92a of the upper side swelling portion 92 is evenly formed and arranged at a position to be substantially flush with an upper surface of the cap 32.

The thickened portion 94 on a lower side is provided in pairs on both end sides in a longitudinal direction of the slit 86. In the case where the valve body 36 is looked from underneath (refer to FIG. 5B), each of the thickened portions 94 is formed in a semi-elliptical shape having an arcuate outer wall 94a on an outer side and a linear wall 94b on an inner side (a side where the slit 86 is formed). A pair of the walls 94b faces each other across the slit 86. The thickened portion 94 protrudes in a direction opposite (downward) to the upper side swelling portion 92 for a predetermined amount, and accordingly a wall thickness of the deformed portion 88 is further increased. Therefore, the entire strength of the valve body 36 is enhanced by the thickened portion 94.

A pair of the walls 94b extends parallel to each other in a direction perpendicular in a longitudinal direction of the slit 86 and extends through near both ends in a longitudinal direction of the slit 86. The pair of walls 94b is arranged upright in an orthogonal direction from a forming surface (bottom surface) of the slit 86 by forming a protrusion on the thickened portion 94, and can help prevent breaking of the valve body 36 along the slit 86.

The guide portion 96 is thinly formed in comparison with the thickened portion 94 and extending in an opening/closing direction of the slit 86, for example, in a separating direction of a pair of the slit walls 86a and 86b, so as to intervene between a pair of the thickened portions 94. In accordance with an exemplary embodiment, the guide portion 96 is corresponding to a portion formed by notching the deformed portion 88, which has a sufficient thickness, along an opening/closing direction of the slit 86.

The guide portion 96 has a function to improve openability of the slit 86 by being thinly formed relative to the thickened portion 94. For example, when the male connector 100 is inserted, a wall of the valve body 36 in a vicinity of the slit 86 is facilitated deformation so as to move to a thinner wall side. Therefore, a pair of the slit walls 86a and 86b easily move toward each other in a separating direction.

In addition, a bottom surface of the deformed portion 88 including the guide portion 96 is formed as a slope 96a in a tapered shape in which a wall thickness of the valve body 36 is gradually reduced along an opening/closing direction from the slit 86. A wall thickness on an outer side in the opening/closing direction of the slit 86 is thinner than a wall thickness in a vicinity of a portion (a center portion) where the slit 86 is formed. The slope 96a can mutually and easily separate bottom surfaces of the deformed portion 88 to be divided by the slit 86, and the slit 86 is more easily opened.

The valve body 36 and the connector 10 according to the present embodiment are basically configured as described above. Hereinafter, a function and an effect thereof will be described.

As described above, in the connector 10, the first tube 12a is connected to the first port 24 on an upper stream side. The first infusion solution is circulated along the main line flow channel 50 in a state in which the second tube 12b is connected to the second port 26 on a downstream side. Therefore, the internal flow channel 52 and the through hole 76 in the connector 10 are filled with the first infusion solution circulating in the main line flow channel 50. The male connector 100 of the third tube 12c is inserted into the third port 28 of the connector 10 in such a state.

As illustrated in FIG. 4, in the insertion, the insertion cylinder 102 comes into contact with the valve body 36 by moving the male connector 100 downward with facing to an upper surface 92a of the valve body 36 (upper side swelling portion 92) in which a head of the insertion cylinder 102 of the male connector 100 is covered by the cap 32. The valve body 36 is pushed downward by further moving the male connector 100 downward (inside the connector 10). As illustrated in FIG. 6A, the valve body 36 is displaced downward relative to the cap 32 by being pushed downward. In this case, the valve body 36 is moved in an opening/closing direction of the slit 86 on a bottom surface side thereof based on a slope of the slope 96a, and a pair of the slit wall 86a and 86b is separated from the bottom surface side. By separating between a pair of the slit walls 86a and 86b, the first infusion solution filled in the through hole 76 moves on the male connector 100 side. As a result, the through hole 76 of the connector 10 has a space, and the male connector 100 can be smoothly inserted.

When the male connector 100 is pushed downward, as illustrated in FIG. 6B, the deformed portion 88 come off from the opening 40 of the cap 32. Therefore, the slit 86 is automatically facilitated to open. In addition, based on elastic deformation of the deformed portion 88, a wall of the deformed portion 88 moves to an outer side in an opening/closing direction along the guide portion 96. As a result, a pair of the slit walls 86a and 86b can separate from each other, and the through hole 76 and the flow path 106 can be easily interconnected.

When the projection 108 of the male connector 100 is screwed together with the ridge 70b on an outer peripheral surface of the cap 32, the male connector 100 moves forward to the connector 10. As a result, as illustrated in FIG. 6C, the third tube 12c and the connector 10 are interconnected. In such a state, the slit 86 widely opens, and the through hole 76 and the flow path 106 are interconnected. The second infusion solution from a separate line smoothly flows in the connector 10.

In addition, the strength of the valve body 36 is improved by the thickened portion 94. Therefore, even in a state in which the valve body 36 is elastically deformed, damage on the valve body 36 can be prevented, and an elastic force thereof can be successfully maintained. If the valve body 36 breaks along a longitudinal direction of the slit 86 with opening the slit 86, the wall 94b of the valve body 36 effectively stop progression of the break.

When the male connector 100 is separated (moved backward) from the connector 10, the valve body 36, which has deformed, is positively and elastically restored and displaced in a separating direction (upward) of the male connector 100. By the elastic restoration, the deformed portion 88 enters into the opening 40 of the cap 32, and a pair of the slit walls 86a and 86b contacts to each other and closes the slit 86. As a result, the through hole 76 is promptly blocked, and leakage of infusion solution from the connector 10 can be prevented.

In addition, the valve body 36 is subjected to a fluid pressure from the first infusion solution flowing into the through hole 76 in a state in which the slit 86 is closed. In this case, since a bottom surface of the deformed portion 88 includes a pair of the slopes 96a, the fluid pressure is received at an angle. Therefore, a pair of the slopes 96a can move a wall of the deformed portion 88 close thereto, and press against a pair of the slit walls 86a and 86b in a closing direction. As a result, the slit 86 can be firmly closed.

As described above, in the valve body 36 according to the present embodiment and the connector 10 including the valve body 36, the slit 86 opens along the guide portion 96 when the male connector 100 is connected to the connector 10, by including the guide portion 96 which is provided along an opening/closing direction of the slit 86 and facilitates opening and closing of the slit 86. As a result, when the connector 10 and the male connector 100 are connected, the first or second infusion solution is smoothly circulated, and leakage of the first or second infusion solution to the outside of the connector 10 can be prevented. In addition, since the valve body 36 includes the thickened portion 94 protrusively formed on a substantially entire bottom surface of the valve body 36 sandwiched between the slit 86 and the guide portion 96, the entire durability of the valve body 36 is improved, and damage on the valve body 36 can be dramatically suppressed. For example, since the thickened portion 94 is disposed in a vicinity of both ends in a longitudinal direction of the slit 86, a break in the longitudinal direction of the slit 86 can be successfully prevented.

The thickened portion 94 includes the wall 94b linearly extending in a direction perpendicular to a longitudinal direction of the slit 86, and thus opening and closing of the slit 86 can be guided along the wall 94b. In addition, for example, if the slit 86 breaks in a direction different from a longitudinal direction of the slit 86, the linearly extending wall 94b can easily block the break.

In accordance with an exemplary embodiment, the connector 10 according to the present disclosure is not limited to a configuration described above and can be applied to various configurations. For example, the connector 10 including the valve body 36 is not limited to a T-port connector as described above. The connector 10 can apply a T-shape stopcock, which can switch a flow channel by rotational displacement of a cork.

Figure 7:
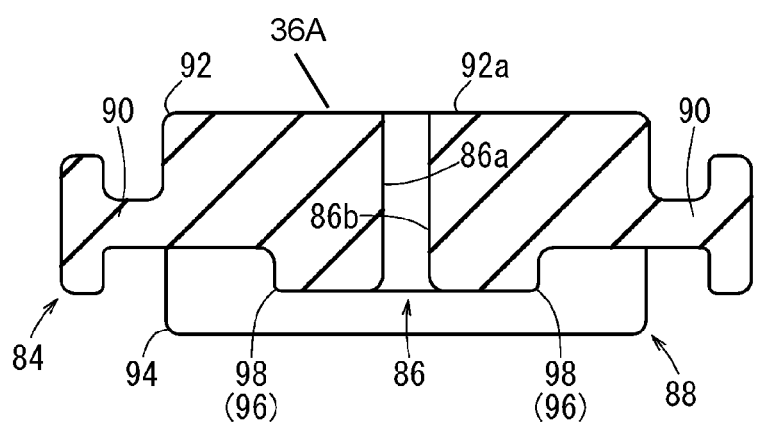
FIG. 7 is a side sectional view illustrating a valve body according to a variation.

In addition, the valve body 36A according to a variation illustrated in FIG. 7 may be arranged to the connector 10. The valve body 36A is formed to a step 98 in which the guide portion 96 (including the slit 86) sandwiched between a pair of the thickened portions 94 has a different thickness. For example, the step 98 is thickly formed in a vicinity of a portion where the slit 86 is formed, and thinly formed on an outer side in an opening/closing direction of the slit 86. Thus, the deformed portion 88 gradually becomes thin toward an outer side in a radial direction. Even if the guide portion 96 is formed as the step 98 as described above, while the valve body 36A is elastically deformed, a wall in a vicinity of a portion where the slit 86 is formed can be moved to an outer side in an opening/closing direction, and the slit 86 can be facilitated to open. In addition, the valve body 36A is subjected to a fluid pressure at the step 98 in a state in which the slit 86 is closed. Therefore, the valve body 36A presses a pair of the slit walls 86a and 86b in a closing direction and more firmly closes the slit 86.

The detailed description above describes a valve body and connector including the same. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A connector comprising:
a main body including a flow channel configured to circulate a fluid, and a space connecting to the flow channel;
a disk shaped valve body including a base body displaceably provided to the space, and a slit which can be opened and closed to the flow channel based on elastic deformation of the base body caused by insertion of a connection into the slit; and
wherein the valve body includes an upper side swelling portion on an upper surface side of the base body, a guide portion provided on a lower surface side of the base body along an opening/closing direction of the slit and configured to facilitate opening and closing of the slit, and a pair of thickened portions on the lower surface side of the base body and protruding in a direction downward beyond a lower surface of the guide portion and a lower edge of the slit, and wherein each thickened portion of the pair of thickened portions is arranged only on an opposite end of the slit and has an inner wall extending in a transverse extending direction to a longitudinal direction of the slit, and wherein the each thickened portion of the pair of the thickened portions is arranged on both sides of the guide portion.

2. The connector according to claim 1, wherein in the guide portion, a wall thickness on an outer side in the opening/closing direction of the slit is thinner than a wall thickness in a vicinity of a portion where the slit is formed.

3. The connector according to claim 2, wherein the guide portion comprises a first guide portion and a second guide portion, and wherein the each of the first guide portion and the second guide portion has a tapered lower surface in which a wall thickness of the valve body is gradually reduced from the slit toward the outer side in the opening/closing direction.

4. The connector according to claim 1, wherein the inner wall of the each thickened portion of the pair of the thickened portions is a wall linearly extending in a direction perpendicular to the transverse extending direction of the slit.

5. The connector according to claim 1, wherein the each thickened portion of the pair of the thickened portions has a semi-elliptical shape having an arcuate outer wall on an outer side and a linear inner wall on an inner side.

6. The connector according to claim 1, wherein the each thickened portion of the pair of the thickened portions has a planar lower surface.

7. The connector according to claim 1, wherein the base body further includes a fixed portion surrounding the base body, and a constriction portion having a wall thickness, the wall thickness of the constriction portion being thinner than a wall thickness of the fixed portion, and wherein the constriction portion is located between the fixed portion and the base body.

8. An infusion set comprising:
the connector according to claim 1;
a first tube connected to a first port of the connector and configured to allow a first infusion solution to flow from the first tube through the first port to the flow channel; and
a second tube connected to the second port of the connector and configured to allow the first infusion solution to flow from the flow channel through the second port and the second tube.

9. The infusion set according to claim 8, comprising:
a third tube connected to a third port, which includes the valve body and configured to allow a second infusion solution to flow from the third tube through the third port to the flow channel.

10. The infusion set according to claim 9, wherein the third tube includes the connection for opening the slit of the valve body when the third tube is connected to the third port.

11. A valve body comprising:
a base body having an upper side swelling portion, a guide portion, and pair of thickened portions, the upper side swelling portion being on an upper surface side of the base body;
an operable and closable slit provided to the base body, the operable and closable slit configured to receive a tube, which physically deforms the base body;
the guide portion being provided on a lower surface side of the base body along an opening/closing direction of the slit and configured to facilitate opening and closing of the slit;
the pair of thickened portions located on the lower surface side of the base body and protruding in a direction downward beyond a lower surface of the guide portion and a lower edge of the slit, and wherein each thickened portion of the pair of thickened portions is arranged only on an opposite end of the slit and has an inner wall extending in a transverse extending direction to a longitudinal direction of the slit, and wherein the each thickened portion of the pair of the thickened portions is arranged on both sides of the guide portion;
a fixed portion surrounding the base body; and
a constriction portion located between the fixed portion and the base body portion, and wherein the constriction portion has a wall thickness, which is thinner than a wall thickness of the fixed portion.

12. The valve body according to claim 11, wherein in the guide portion, a wall thickness on an outer side in the opening/closing direction of the slit is thinner than a wall thickness in a vicinity of a portion where the slit is formed.

13. The valve body according to claim 12, wherein the guide portion comprises a first guide portion and a second guide portion, and wherein the each of the first guide portion and the second guide portion has a tapered lower surface in which a wall thickness of the valve body is gradually reduced from the slit toward the outer side in the opening/closing direction.

14. The valve body according to claim 11, wherein the inner wall of the each thickened portion of the pair of the thickened portions is a wall linearly extending in a direction perpendicular to the transverse extending direction of the slit.

15. A connector comprising:
a flow channel configured to circulate a fluid;
a disk shaped valve body including a displaceable base body; and
a slit which can be opened and closed to the flow channel based on elastic deformation of the base body caused by insertion of a connection into the slit, wherein the valve body includes an upper side swelling portion on an upper surface side of the base body, a guide portion provided on a lower surface side of the base body along an opening/closing direction of the slit and configured to facilitate opening and closing of the slit, and a pair of thickened portions on the lower surface side of the base body and protruding in a direction downward beyond a lower surface of the guide portion and a lower edge of the slit, and wherein each thickened portion of the pair of thickened portions is arranged only on an opposite end of the slit and has an inner wall extending in a transverse extending direction to a longitudinal direction of the slit, and wherein the each thickened portion of the pair of the thickened portions is arranged on both sides of the guide portion.

16. The connector according to claim 15, wherein in the guide portion, a wall thickness on an outer side in the opening/closing direction of the slit is thinner than a wall thickness in a vicinity of a portion where the slit is formed.

17. The connector according to claim 16, wherein the guide portion comprises a first guide portion and a second guide portion, and wherein the each of the first guide portion and the second guide portion has a tapered lower surface in which a wall thickness of the valve body is gradually reduced from the slit toward the outer side in the opening/closing direction.

18. The connector according to claim 15, wherein the inner wall of the each thickened portion of the pair of the thickened portions is a wall linearly extending in a direction perpendicular to the transverse extending direction of the slit.

19. The connector according to claim 15, further comprising:
a circularly formed fixed portion surrounding the base body; and
a constriction portion located between the fixed portion and the base body portion, and wherein the constriction portion has a wall thickness, which is thinner than a wall thickness of the fixed portion.

20. An infusion set comprising:
the connector according to claim 15;
a first tube connected to a first port of the connector and configured to allow a first infusion solution to flow from the first tube through the first port to the flow channel; and
a second tube connected to the second port of the connector and configured to allow the first infusion solution to flow from the flow channel through the second port and the second tube; and
a third tube connected to a third port, which includes the valve body and configured to allow a second infusion solution to flow from the third tube through the third port to the flow channel.

* * * * *